(12) United States Patent
Hardimon et al.

(10) Patent No.: US 11,148,990 B2
(45) Date of Patent: Oct. 19, 2021

(54) MAGNESIUM CITRATE GLYCINATE CO-SALT

(71) Applicant: JOST CHEMICAL CO., St. Louis, MO (US)

(72) Inventors: Joseph R. Hardimon, Belleville, IL (US); Kasey L. Morris, Florissant, MO (US)

(73) Assignee: Jost Chemical Co., St. Louis, MO (US)

( * ) Notice: Subject to any disclaimer, the term of this patent is extended or adjusted under 35 U.S.C. 154(b) by 0 days.

(21) Appl. No.: 17/112,164

(22) Filed: Dec. 4, 2020

(65) Prior Publication Data

US 2021/0188755 A1 Jun. 24, 2021

Related U.S. Application Data

(60) Provisional application No. 62/951,724, filed on Dec. 20, 2019.

(51) Int. Cl.
*C07C 51/41* (2006.01)
*C07C 227/18* (2006.01)
(Continued)

(52) U.S. Cl.
CPC ............ *C07C 51/41* (2013.01); *C07C 227/18* (2013.01); *C07F 3/02* (2013.01); *C07C 59/245* (2013.01); *C07C 229/08* (2013.01)

(58) Field of Classification Search
None
See application file for complete search history.

(56) References Cited

U.S. PATENT DOCUMENTS 6,197,815 B1 * 3/2001 Hsu ...................... A23K 20/105
514/502
2005/0220865 A1 10/2005 Koleng et al.

OTHER PUBLICATIONS

International Search Report for PCT/US2020/063301 dated Mar. 3, 2021.
Written Opinion for PCT/US2020/063301 dated Mar. 3, 2021.

* cited by examiner

*Primary Examiner* — Amy C Bonaparte
(74) *Attorney, Agent, or Firm* — Sandberg Phoenix & von Gontard, P.C.

(57) ABSTRACT

A magnesium citrate glycinate co-salt has a formula of $Mg_2C_8H_9NO_9$—$XH_2O$ and a suggested structure of:

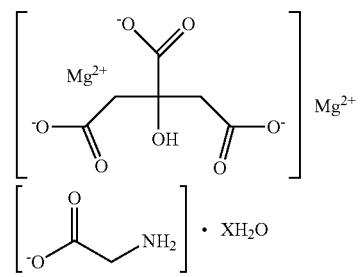

The magnesium citrate glycinate co-salt has an apparent density of 1740 kg/m$^3$ and is compressible in a range of compression pressures from approximately 50 MPa to approximately 150 MPa. The magnesium citrate glycinate co-salt is formed by combining citric acid and glycine in a 1:1 molar ratio to form an aqueous reaction mixture and (Continued)

TGA of Magnesium Citrate Glycinate Co-salt (Sample A)

neutralizing the aqueous reaction mixture with a magnesium source having a magnesium:ligand ratio of 1:1.

8 Claims, 19 Drawing Sheets

(51) Int. Cl.
*C07F 3/02* (2006.01)
*C07C 229/08* (2006.01)
*C07C 59/245* (2006.01)

TGA of the "Component Dry Blend"

FT-IR for Magnesium Bis-glycinate

SEM Imaging of Magnesium Bis-Glycinate

SEM Imaging of Magnesium Citrate Tribasic

SEM Imaging of Magnesium Citrate Glycinate Co-salt

XRD Analysis of Magnesium Citrate Glycinate Co-Salt

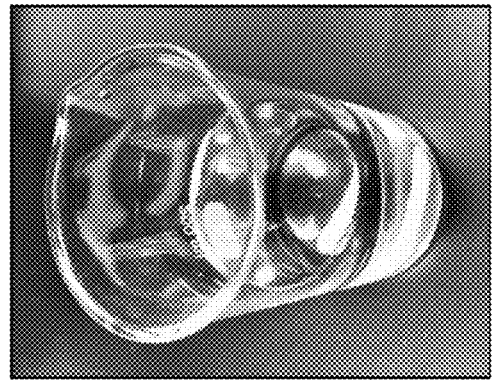
FIG. 21 Di-Magnesium Citrate Glycinate Co-Salt (left) after 24 hours
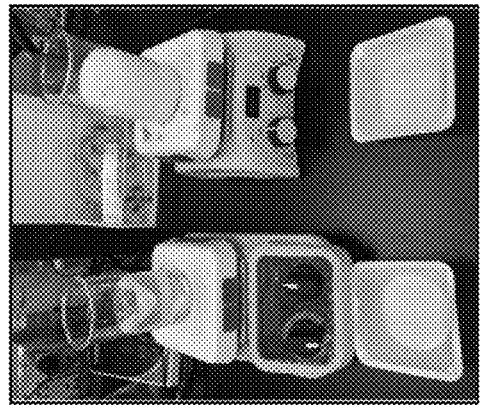
FIG. 20 Di-Magnesium Citrate Glycinate Co-Salt (left) and "Component Dry Blend (right) each in 90 mL water
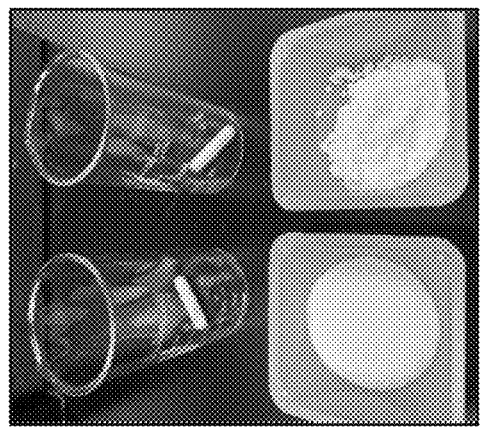
FIG. 19 10g Di-Magnesium Citrate Glycinate Co-Salt (left) and 10g "Component Dry Blend (right)

Compression Profiles of Magnesium Citrate Glycinate Co-salt

MAGNESIUM CITRATE GLYCINATE CO-SALT

CROSS-REFERENCE TO RELATED APPLICATIONS

This application claims priority to U.S. App. No. 62/951,724 filed Dec. 20, 2019, which is entitled Divalent Metal Citrate Glycinate Co-Salts, and which is incorporated herein by reference.

STATEMENT REGARDING FEDERALLY SPONSORED RESEARCH OR DEVELOPMENT

Not Applicable.

BACKGROUND

Use of magnesium citrate and magnesium bis-glycinates salt, either independently or blended, often yield attributes or performance that is less than desirable. Magnesium citrate tribasic exhibits poor aqueous solubility and can be difficult to compress in tableting applications due to low compressibility. Magnesium bis-glycinate has decent aqueous solubility, however, magnesium bis-glycinate salts also exhibit poor compression indices and have a very unpleasant taste profile which can limit their use in foods, beverages, and other oral applications.

BRIEF SUMMARY

A novel concept has been developed in magnesium citrate glycinate co-salt which incorporates an equal molar ratio of citric acid and glycine, completely neutralized with magnesium in a metal to ligand ratio of 2:1:1 (i.e., 2 moles Mg, 1 mole citrate and 1 mole glycinate). This new co-salt mitigates issues regarding poor compressibility and low magnesium loading and improves aqueous solubility and poor organoleptic properties associated with the use of magnesium citrate and magnesium bis-glycinate salts either independently or as blends thereof.

Briefly, the magnesium citrate glycinate co-salt having a formula of $Mg_2C_8H_9NO_9$—$XH_2O$ and a suggested structure of:

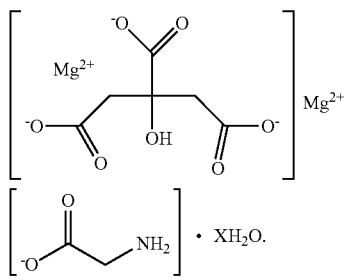

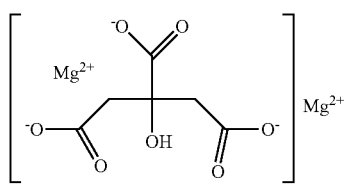

As is readily apparent, in anhydrous form, the magnesium citrate glycinate co-salt will have a formula of $Mg_2C_8H_9NO_9$ and a suggested structure of:

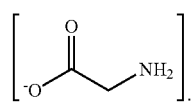

The magnesium citrate glycinate co-salt has an apparent density of 1740 kg/m³.

The magnesium citrate glycinate co-salt is compressible in a range of compression pressures from approximately 50 MPa to approximately 150 MPa.

The magnesium citrate glycinate co-salt is prepared by combining citric acid and glycine in a 1:1 molar ratio to form an aqueous reaction mixture of citric acid and glycine solution and then neutralizing the aqueous reaction mixture with a magnesium source having a magnesium:ligand ratio of 1:1.

The magnesium source can be magnesium, a magnesium oxide, a magnesium hydroxide, or a magnesium carbonate. The reaction mechanism for producing the co-salt being:

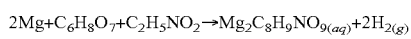

—or—

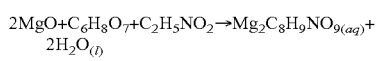

—or—

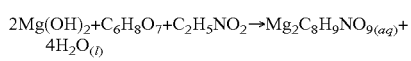

—or—

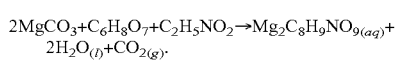

The neutralization step includes neutralizing the 1:1 molar ratio of citric acid and glycine aqueous solution to a pH between 8.5-10.5 to form a neutralized solution.

The neutralized solution can then be dried to a free-flowing powder.

To demonstrate the unique nature of the magnesium citrate glycinate co-salt, attempts to produce other divalent metal to ligand ratio 2:1:1 co-salts were unsuccessful. These divalent metals include calcium, copper, and zinc in which the insoluble divalent metal tribasic citrate salt is precipitated when the reaction pH is taken through the $2^{nd}$ pKa of citric acid (pH=4.8), leaving the glycine solubilized in the mother liquors. Experiments using iron and manganese were also unsuccessful due to rapid oxidation of the metals in the reaction mass when approaching the pH needed to completely neutralize the acid solution. These reactions were obviously terminated due to the non-divalent nature of the products being produced.

BRIEF DESCRIPTION OF THE DRAWINGS

FIG. 19 is a photograph of magnesium citrate glycinate co-salt (left) and the "Component Dry Blend (right);

FIG. 20 is a photograph of magnesium citrate glycinate co-salt (left) and "Component Dry Blend (right) each in water;

FIG. 21 is a photograph of magnesium citrate glycinate co-salt (left) after 24 hours in water;

Corresponding reference numerals will be used throughout the several figures of the drawings.

DETAILED DESCRIPTION

Figure 1:
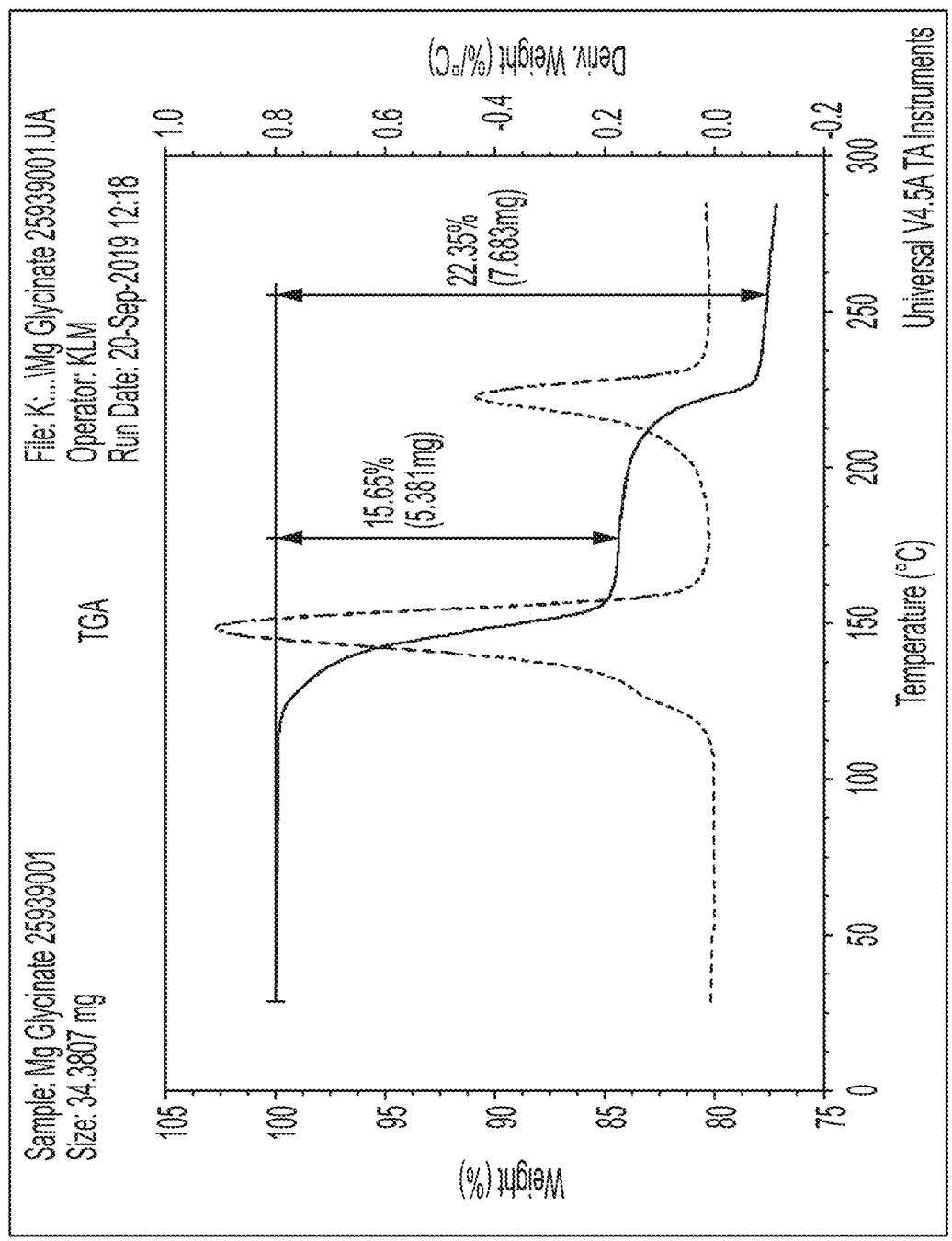
FIGS. 1-3 show Thermogravimetric Analysis (TGA) patterns for magnesium bis-glycinate, magnesium citrate tribasic, and a "component dry blend" of magnesium bis-glycinate and magnesium citrate tribasic.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Several laboratory samples of magnesium citrate glycinate co-salt were prepared for use in demonstrating both matter of composition and comparative studies against both magnesium citrate tribasic and magnesium bis-glycinate.

Magnesium citrate glycinate co-salt when prepared correctly has a molecular formula of $Mg_2C_8H_9NO_9$—$XH_2O$ as shown in production of an aqueous solution in Equation 1 and by drying to a free-flowing powder in Equation 2.

$$2MgO + C_6H_8O_{7(aq)} + C_2H_5NO_{2(aq)} \rightarrow Mg_2C_8H_9NO_{9(aq)} + 2H_2O_{(l)} \quad \text{Equation 1:}$$

$$Mg_2C_8H_9NO_{9(aq)} \rightarrow Mg_2C_8H_9NO_9 - XH_2O \text{ (Drying Step)} \quad \text{Equation 2:}$$

It is believed that the magnesium citrate glycinate co-salt has the following structure:

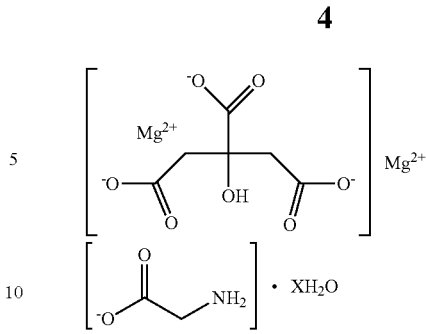

The source for the magnesium can be magnesium oxide (as shown above in Equation 1). Alternatively, the magnesium source can be magnesium, a magnesium hydroxide or carbonate (i.e., Mg, $Mg(OH)_2$ or $MgCO_3$). In this case, Equation 1 would be shown be Equation 1 b-1d below:

$$2Mg + C_6H_8O_7 + C_2H_5NO_2 \rightarrow Mg_2C_8H_9NO_{9(aq)} + 2H_{2(g)} \quad \text{Equation 1 b:}$$

$$2Mg(OH)_2 + C_6H_8O_7 + C_2H_5NO_2 \rightarrow Mg_2C_8H_9NO_{9(aq)} + 4H_2O_{(l)} \quad \text{Equation 1c:}$$

$$2MgCO_3 + C_6H_8O_7 + C_2H_5NO_2 \rightarrow Mg_2C_8H_9NO_{9(aq)} + 2H_2O_{(l)} + CO_{2(g)} \quad \text{Equation 1d.}$$

Magnesium citrate glycinate co-salt has a molecular weight of 311.8 g/mol and magnesium content of 15.6% on an anhydrous basis. The co-salt typically is found to contain between 0.0-20.0% water depending on extent of drying.

To demonstrate matter of composition and product superiority, classical chemistry methodology (assay), thermogravimetric analysis (TGA), infrared spectroscopy (FT-IR), X-ray diffraction (XRD), aqueous solubility and organoleptic (taste) testing were implemented.

To assist in matter of composition and comparison, a dry blend was prepared by mixing ½ mole of magnesium citrate tribasic hydrate with ½ mole of magnesium bis-glycinate. This dry blend possesses the same 1:1 metal to ligand molar ratio as does di-magnesium citrate glycinate (2 moles Mg, 1 mole citrate and 1 mole glycinate). This sample will further be referred to as the "component dry blend" and will be used to help demonstrate the novel magnesium citrate glycinate co-salt's composition uniqueness and superiority to individual magnesium citrate tribasic and magnesium bis-glycinate.

Classical Chemistry Methodology

Research samples of magnesium citrate glycinate co-salts (Samples A and B) and pilot scale sample (Sample C) were prepared and analyzed for magnesium content using EDTA titration. The water content of both samples was determined by TGA so that the anhydrous magnesium content could be calculated and compared to theoretical anhydrous magnesium content. The three samples shown in Table 1 all contain the precise theoretical amount of magnesium that is consistent with the di-magnesium citrate glycinate co-salt formula.

TABLE 1

Magnesium Content, Water Content and Theoretical Assay values for Magnesium Citrate Glycinate Co-salts

| Sample | % Mg (as is) | % Water | % Mg Anhydrous | % of Theoretical Mg (15.6%) |
|---|---|---|---|---|
| A | 13.1% | 16.1% | 15.6% | 100.0% |
| B | 12.6% | 19.5% | 15.7% | 100.6% |
| C | 13.2% | 15.7% | 15.7% | 100.6% |

Thermogravimetric Analysis (TGA)

Figure 2:
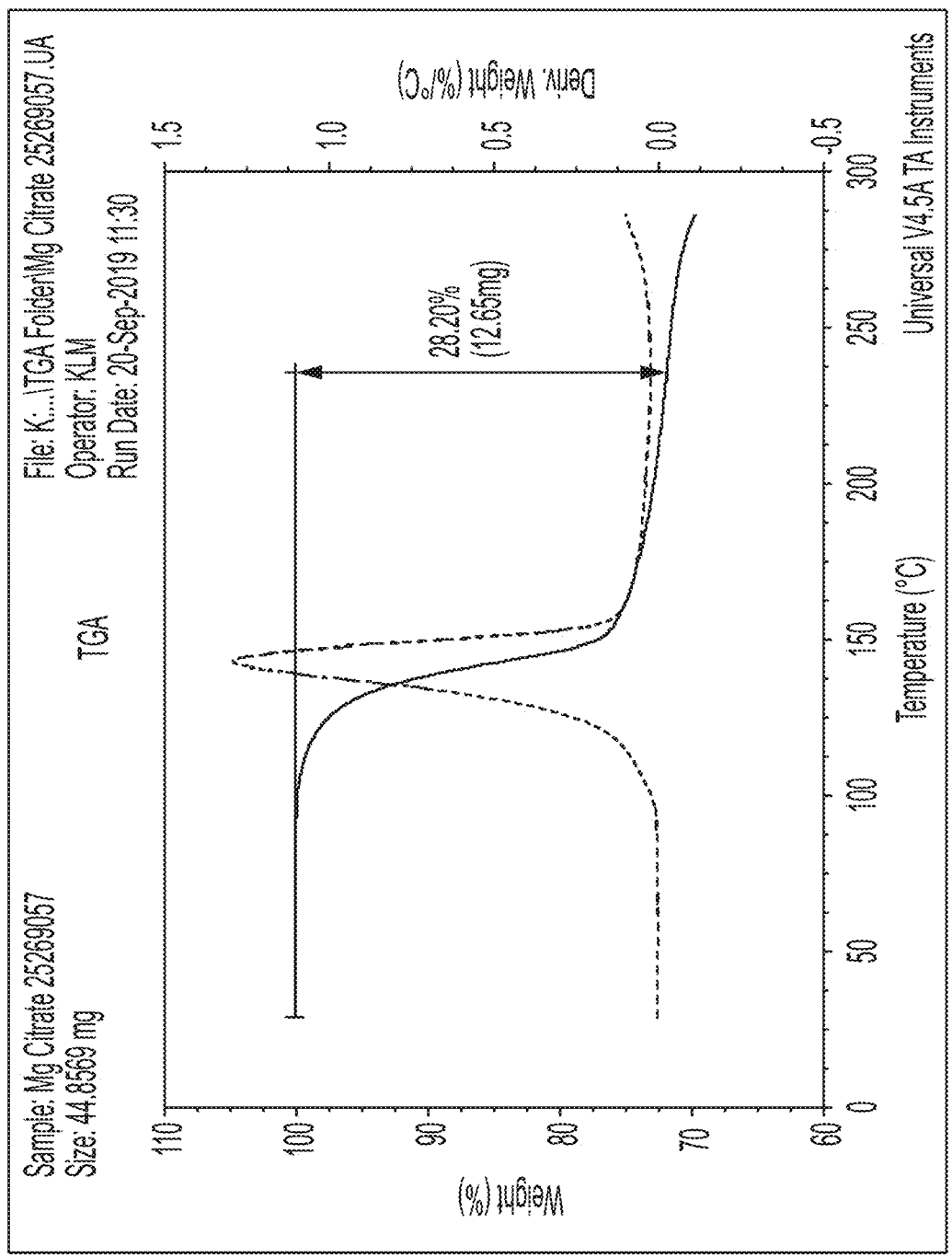
Figure 3:
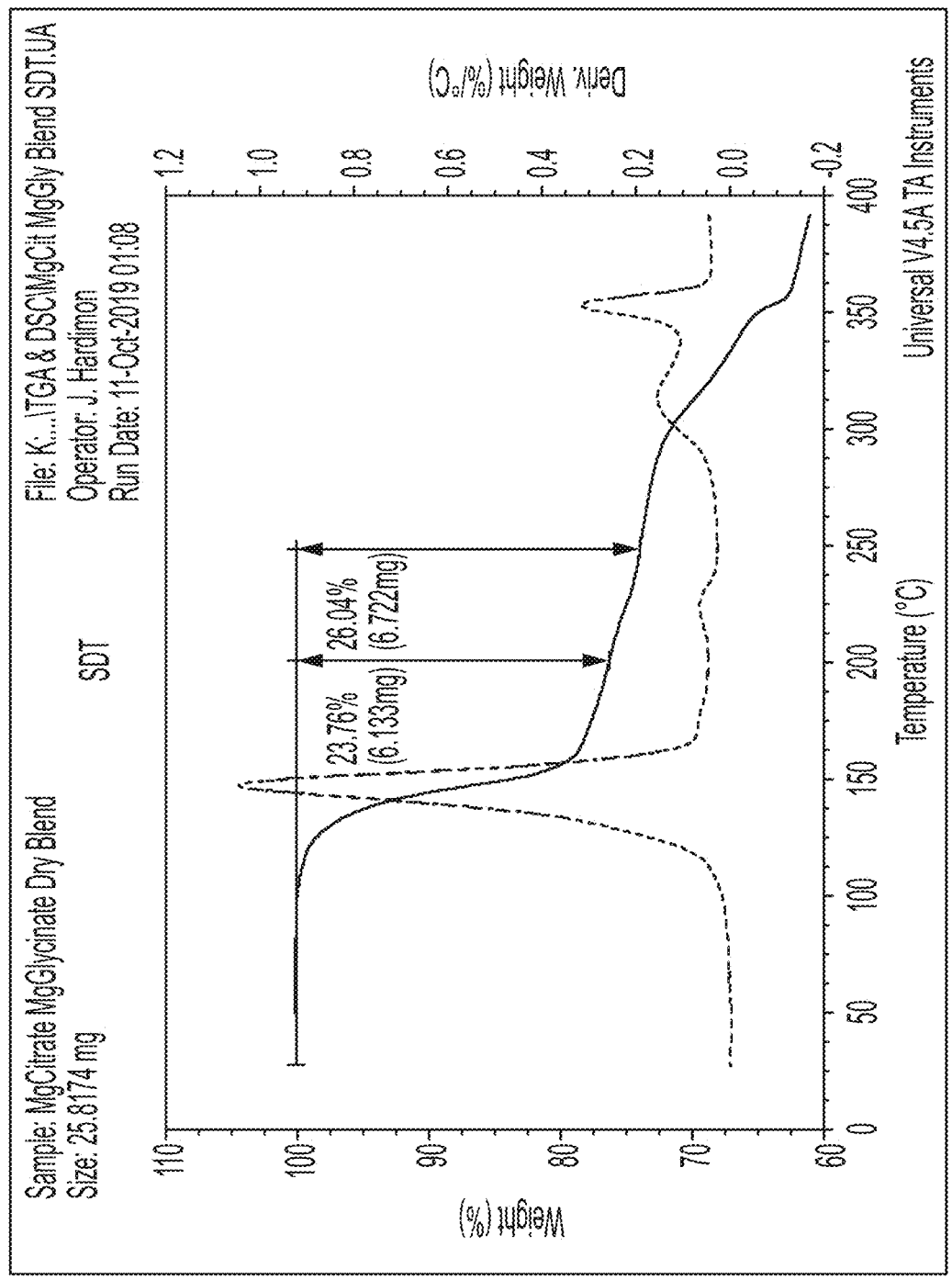

TGA was used not only to accurately determine the water content of the co-salts being produced as shown in Table 1 but was also employed to demonstrate the uniqueness of the co-salt against magnesium citrate tribasic, magnesium bis-glycinate and the "component dry blend" described in the Invention Description. FIGS. 1-3 show the TGA pattern for magnesium bis-glycinate, magnesium citrate tribasic, and the "component dry blend".

One can clearly see in FIGS. 1 and 2 that the TGA patterns for magnesium bis-glycinate and magnesium citrate tribasic are highly ordered and indicative of waters of crystallization being released over a small range of temperature demonstrated by the steep slope of the weight (%) signal. The TGA of the "component dry blend" in FIG. 3 also shows this type of water loss pattern. Those skilled in the art will also recognize that the "component dry blend" TGA shows both magnesium citrate tribasic and magnesium bis-glycinate weight loss events.

Figure 4:
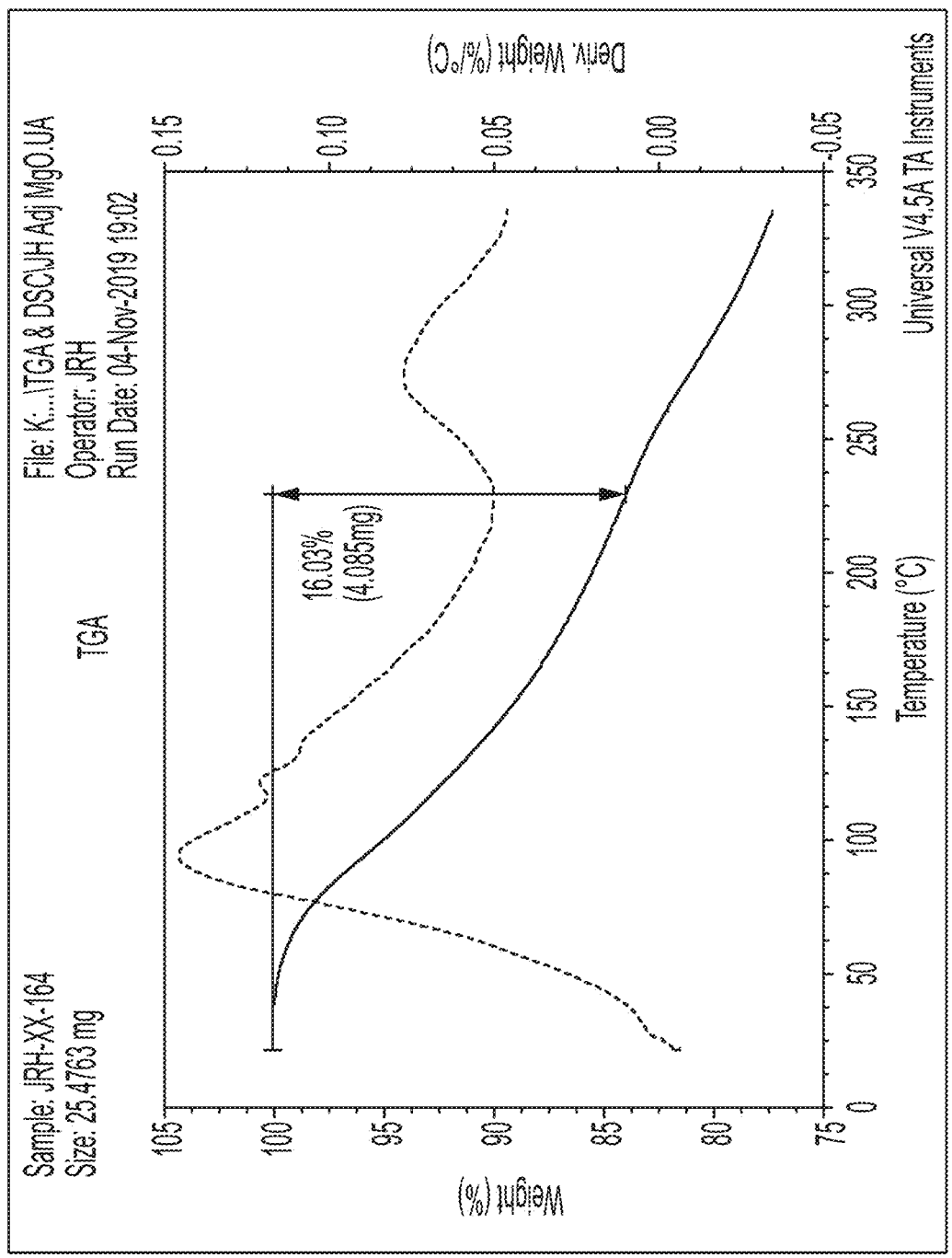
FIG. 4 shows the TGA pattern for a magnesium citrate glycinate co-salt sample.

FIG. 4 shows the TGA pattern for a magnesium citrate glycinate co-salt sample prepared according to the method of Example 1 (below). Clearly, this pattern is different than the patterns seen in FIGS. 1-3, as the weight loss event is happening over a very broad temperature range. These types of TGA patterns are indicative of amorphous solids.

If the co-salt sample were merely a co-precipitation of magnesium citrate and magnesium bis-glycinate, the TGA pattern would look identical to FIG. 3. However, this co-salt technology is not a co-precipitated product of separate magnesium citrate and bis-glycinate components, but a unique chemical entity as demonstrated by comparing FIGS. 3 and 4. That is, the TGA pattern indicates that the product is not a mere mixture of magnesium citrate and bis-glycinate, but rather, a unique compound.

FT-IR Spectroscopy

Figure 5:
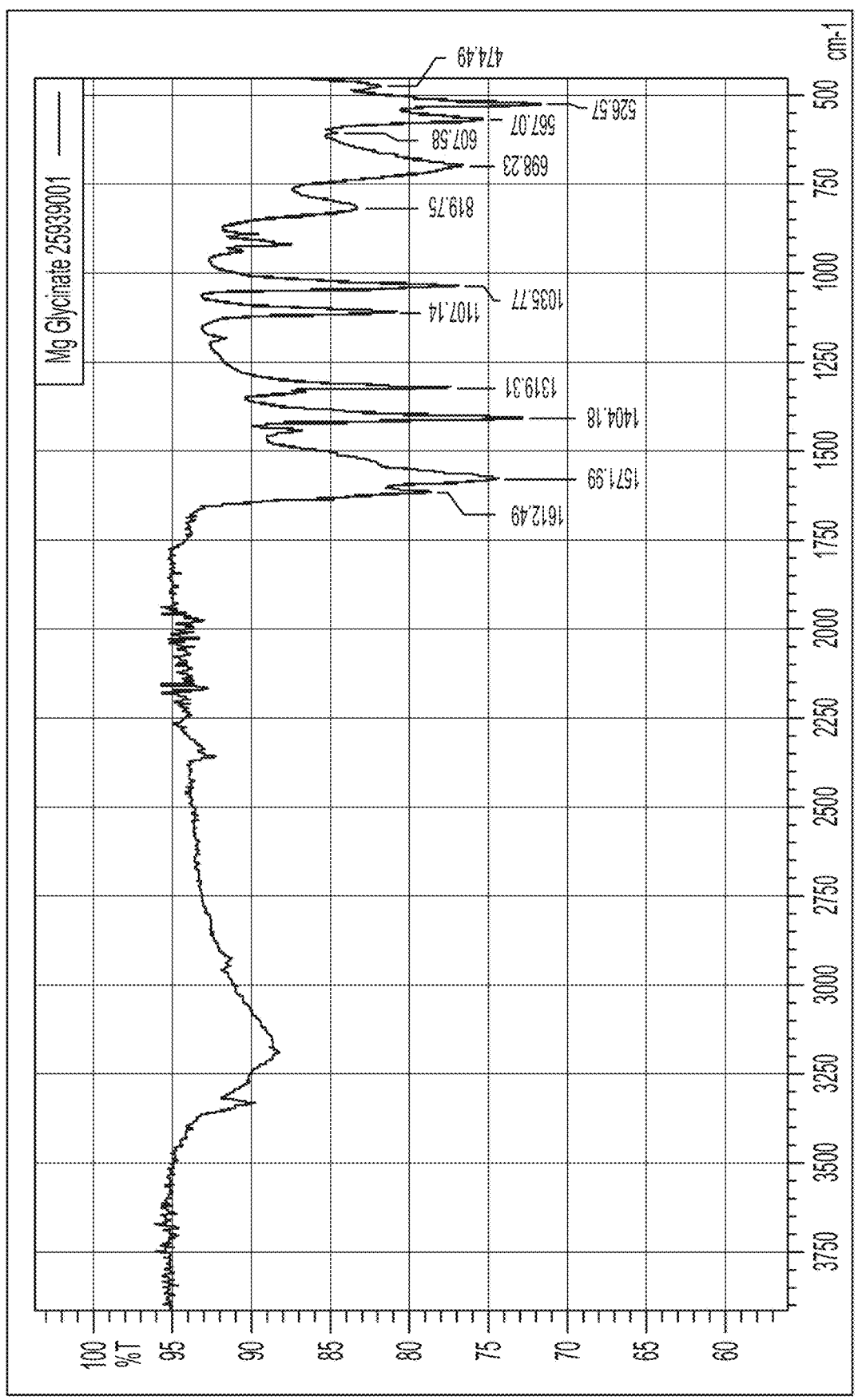
FIGS. 5-7 show the FT-IR spectra for magnesium bis-glycinate magnesium citrate tribasic, and the "component dry blend", respectively.
Figure 6:
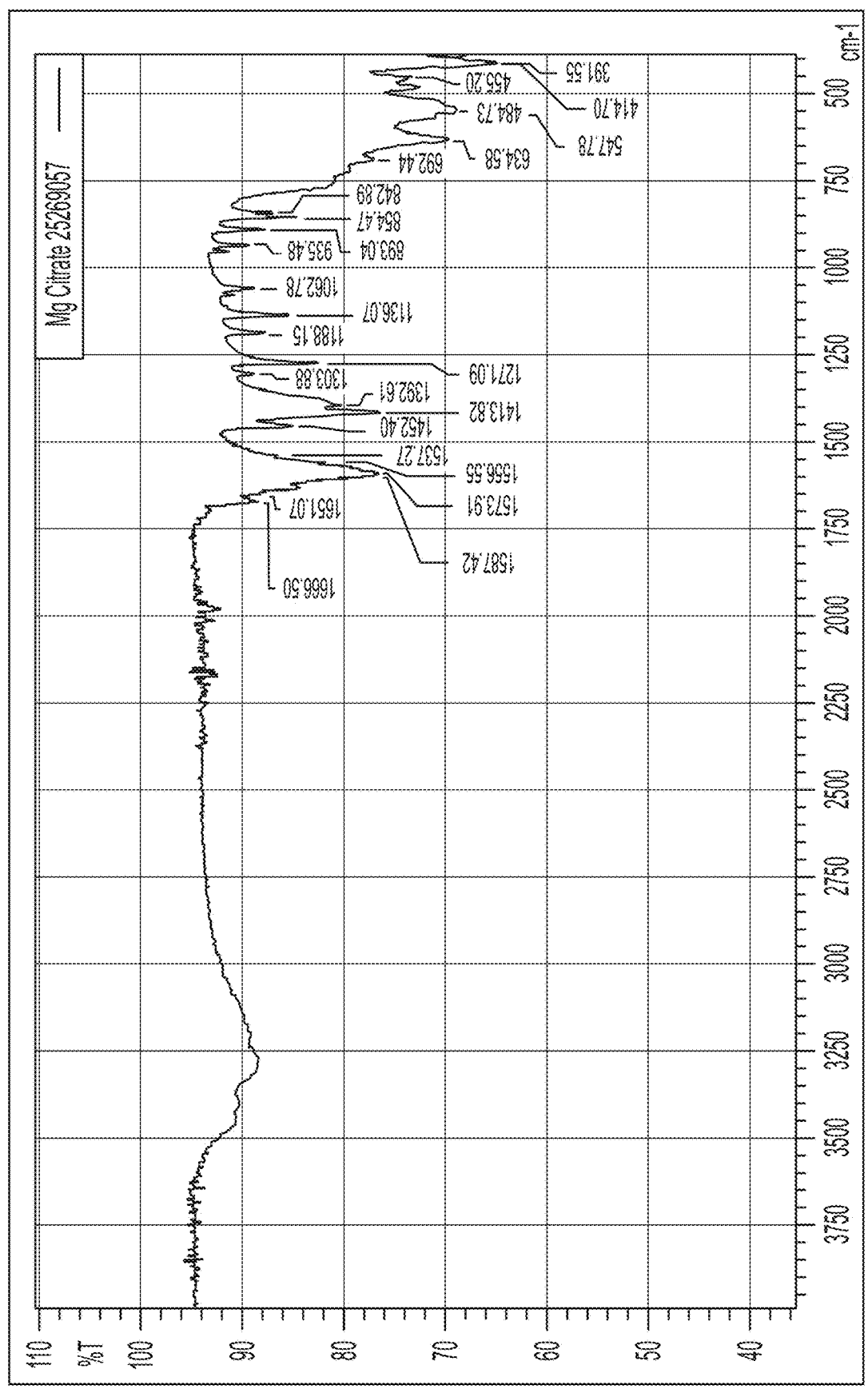
Figure 7:
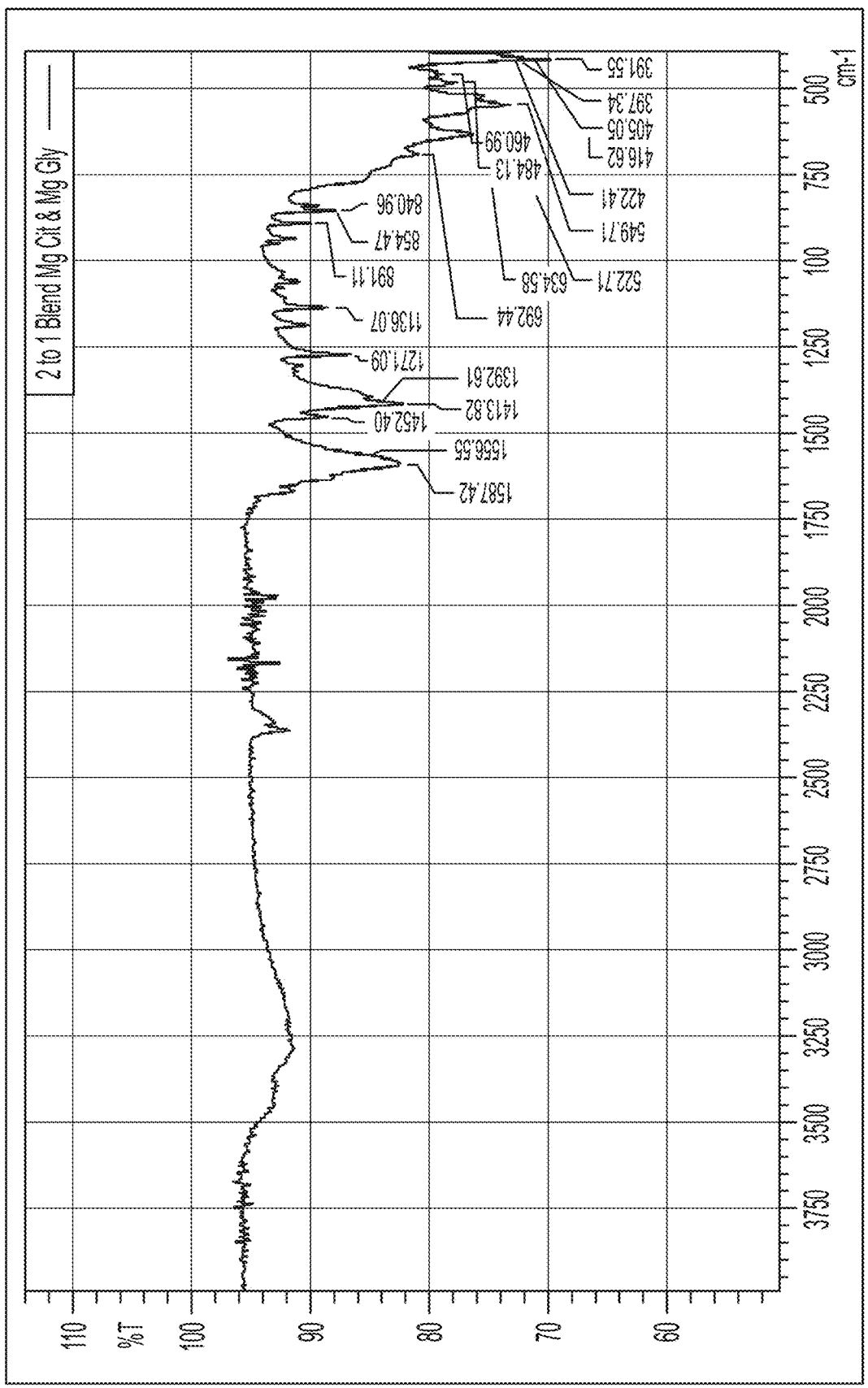

Infrared spectroscopy was also employed to demonstrate the uniqueness of the co-salt against magnesium citrate tribasic, magnesium bis-glycinate and the "component dry blend" described in the Invention Description. FIGS. 5-7 show the FT-IR spectra for magnesium bis-glycinate magnesium citrate tribasic, and the "component dry blend".

Magnesium Bis-glycinate (FIG. 5) shows strong absorbances in the fingerprint region of 1572, 1404, 1319, 1107 and 1036 cm$^{-1}$ and a distribution of strong absorbances between approximately 630 and 820 cm$^{-1}$.

Magnesium Citrate Tribasic (FIG. 6) has strong absorbances in the fingerprint region of 1573, 1413, 1271 and 1140 cm$^{-1}$ and a distribution of weaker less defined absorbances between approximately 391 and 634 cm$^{-1}$ The "Component Dry Blend" (FIG. 7) has strong absorbances in the fingerprint region of 1587, 1413, 1271 and 1136 cm$^{-1}$. Looking closer at its strong absorptions and peak shapes, one skilled in the art would discern that this is indeed a physical blend as both aspects of the independent spectra (FIGS. 5 and 6) are visible yet muted by each other.

Figure 8:
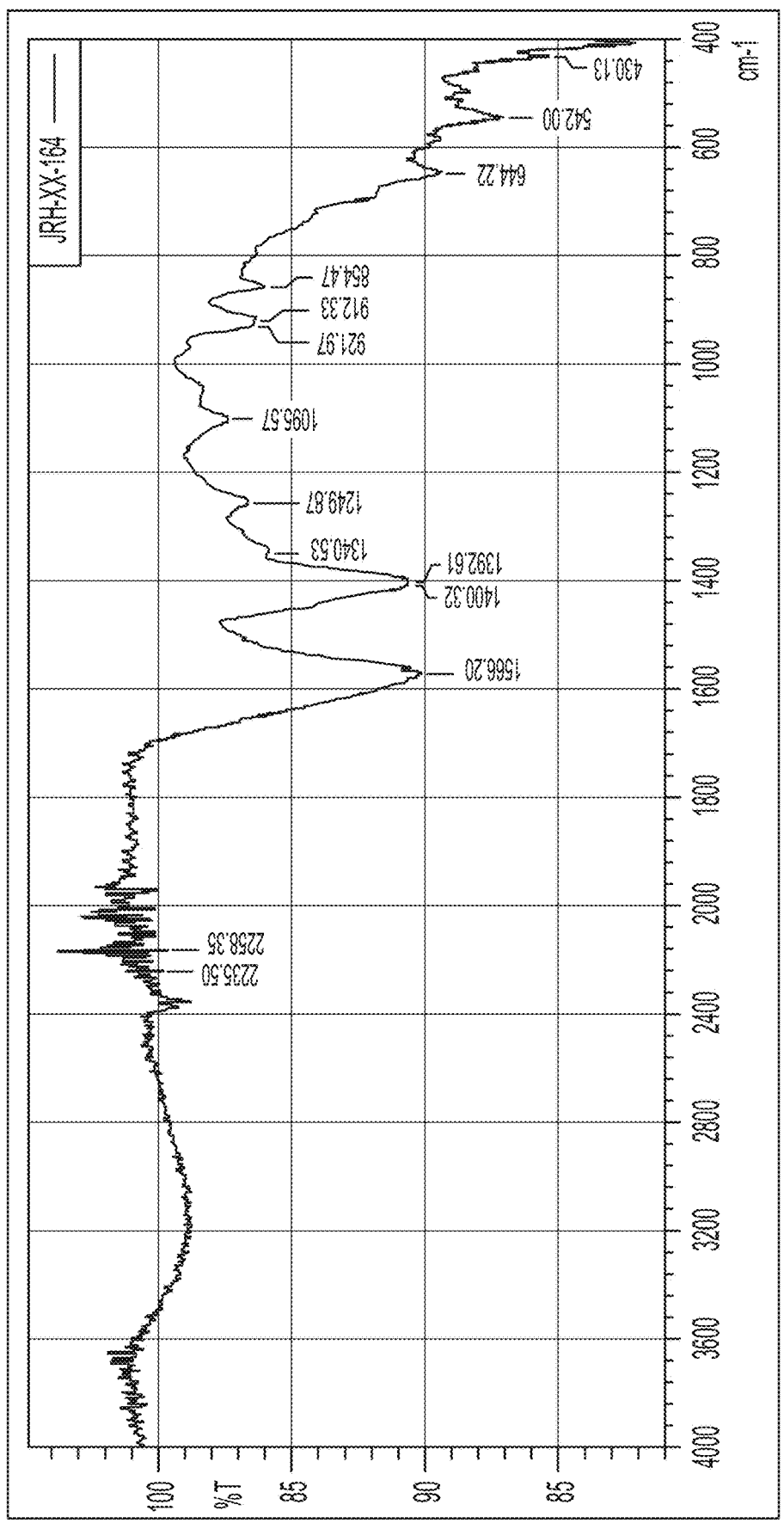
FIG. 8 shows the FT-IR spectrum for the magnesium citrate glycinate co-salt sample.

The Ft-IR spectrum for magnesium citrate glycinate co-salt (Sample A) is shown in FIG. 8. The co-salt has strong absorbances in the fingerprint region of 1566 and 1400 cm$^{-1}$. Take note that the sharp absorbances between 750-1350 cm$^{-1}$ found in FIGS. 5-7 are either gone or have been substantially broadened.

The FT-IR spectra of the "component dry blend" in FIG. 7 and the magnesium citrate glycinate co-salt in FIG. 8 are substantially different, providing strong evidence that the co-salt is a unique entity or compound and not a mere blend or mixture of magnesium citrate and bis-glycinate components.

Particle Morphology by Scanning Electron Microscopy

Figure 9:
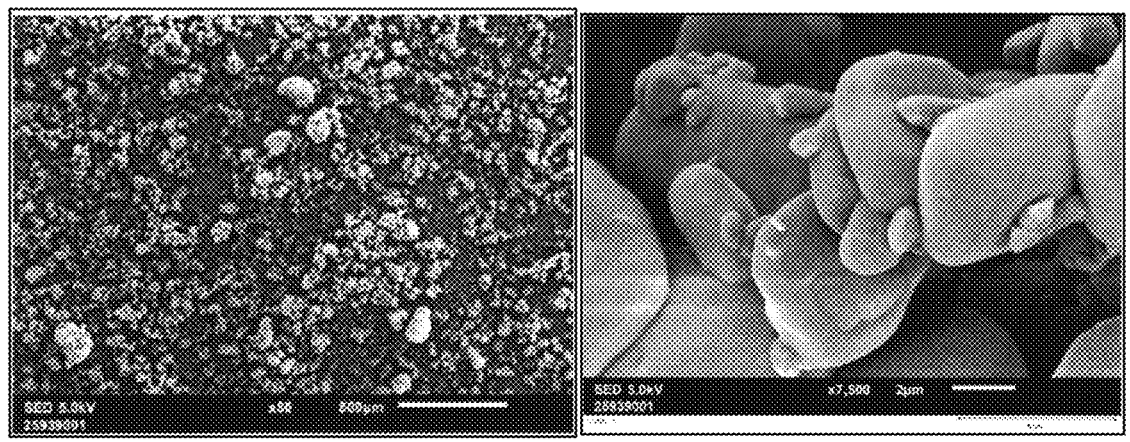
FIGS. 9-11 show SEM (Scanning Electron Microscopy) imaging of magnesium bis-glycinate, magnesium citrate tribasic and magnesium citrate glycinate co-salt, respectively.
Figure 10:
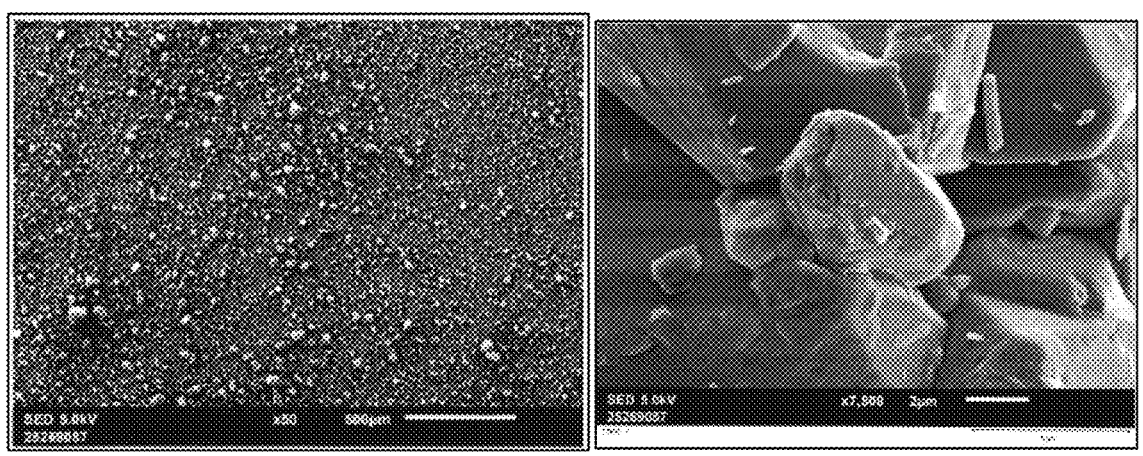
Figure 11:
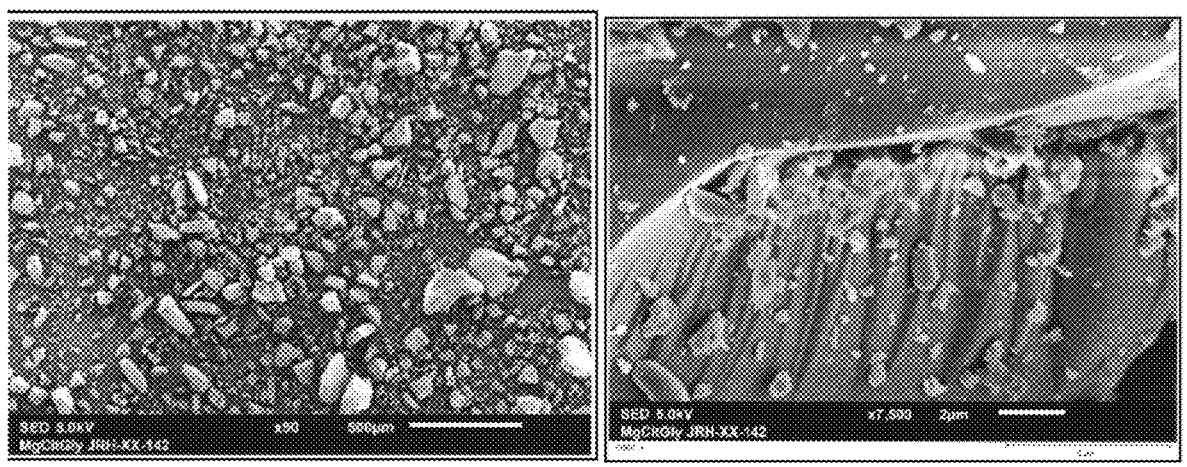

The unique nature of the magnesium citrate glycinate co-salt can be both demonstrated and differentiated form magnesium citrate tribasic and magnesium glycinate. FIGS. 9-11 show SEM (Scanning Electron Microscopy) imaging of magnesium bis-glycinate, magnesium citrate tribasic and magnesium citrate glycinate co-salt respectively.

As shown in FIG. 9, magnesium bis-glycinate has a polycrystalline presentation, composed of many crystallites of varying size and orientation. SEM imaging of magnesium citrate tribasic shown in FIG. 10 shows a singular type of crystallinity dictated by layers of mono/triclinic plates.

SEM imagery of magnesium citrate glycinate co-salt shown in FIG. 11 demonstrates the amorphous nature of this product. Lack of either the polycrystalline crystallites found in magnesium bis-glycinate or triclinic plates found in magnesium citrate tribasic demonstrate that this co-salt is not a mere co-precipitated blend of magnesium citrate and magnesium bis-glycinate, but a unique chemical entity or compound.

X-Ray Diffraction (XRD) Pattern Analysis

Figure 12:
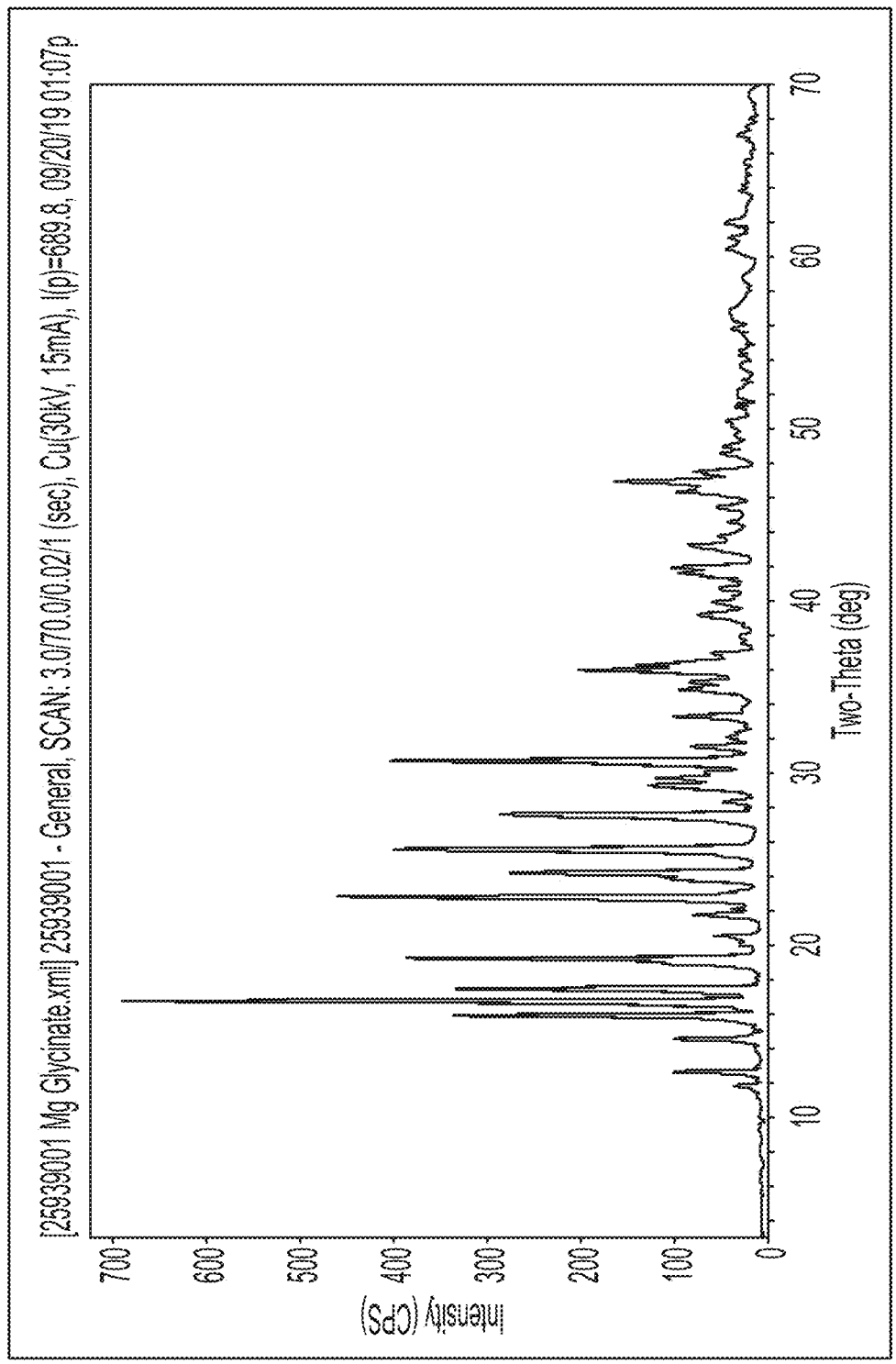
FIGS. 12-14 show XRD patterns for magnesium bis-glycinate, magnesium citrate tribasic, and the "dry blend", respectively.
Figure 13:
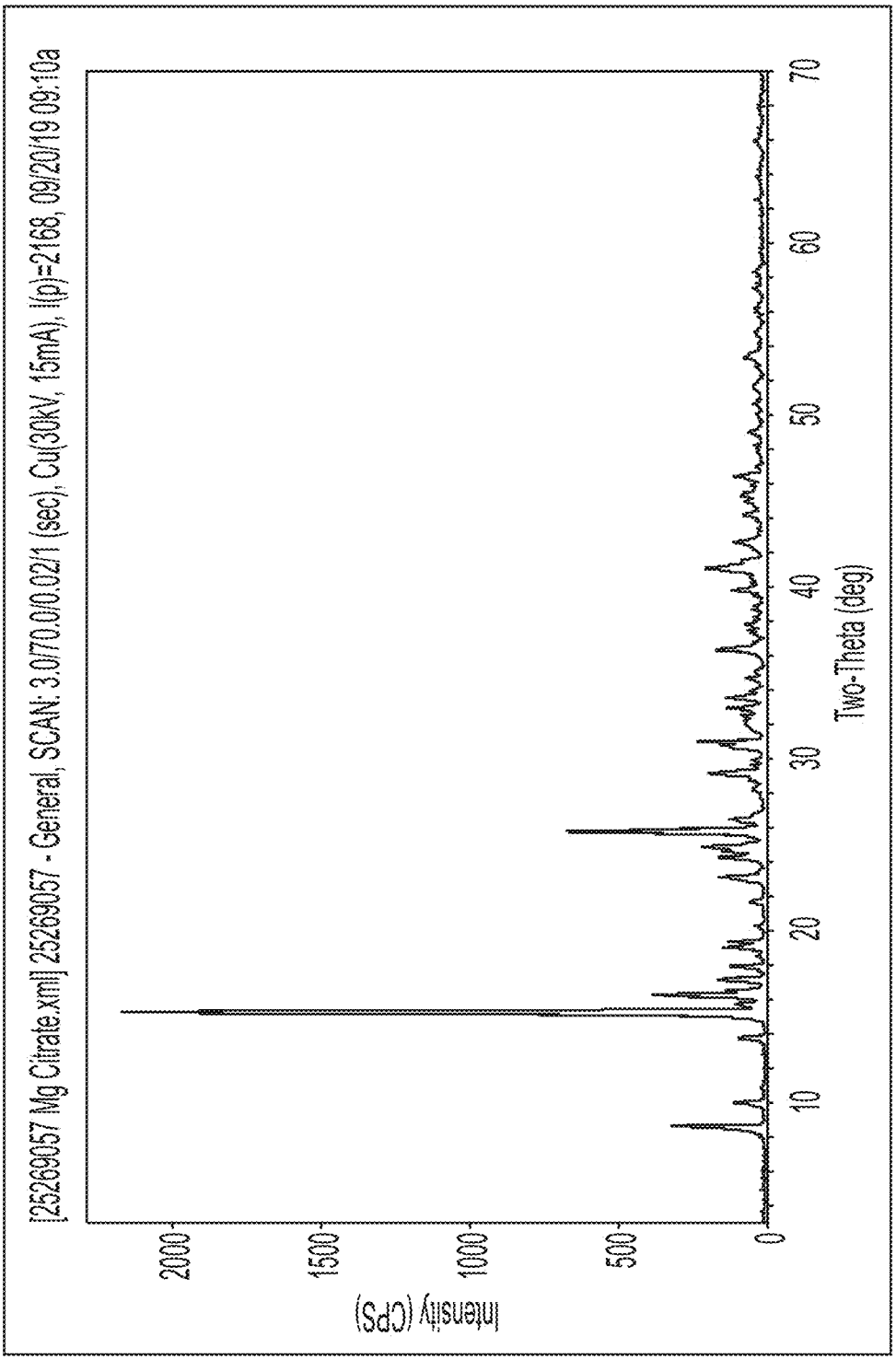

As described in Thermogravimetric Analysis and Particle Morphology by Scanning Electron Microscopy, magnesium bis-glycinate and magnesium citrate tribasic are relatively high crystalline materials and as such have very distinct and reproducible XRD patterns which are shown in FIGS. 12 and 13.

Figure 14:
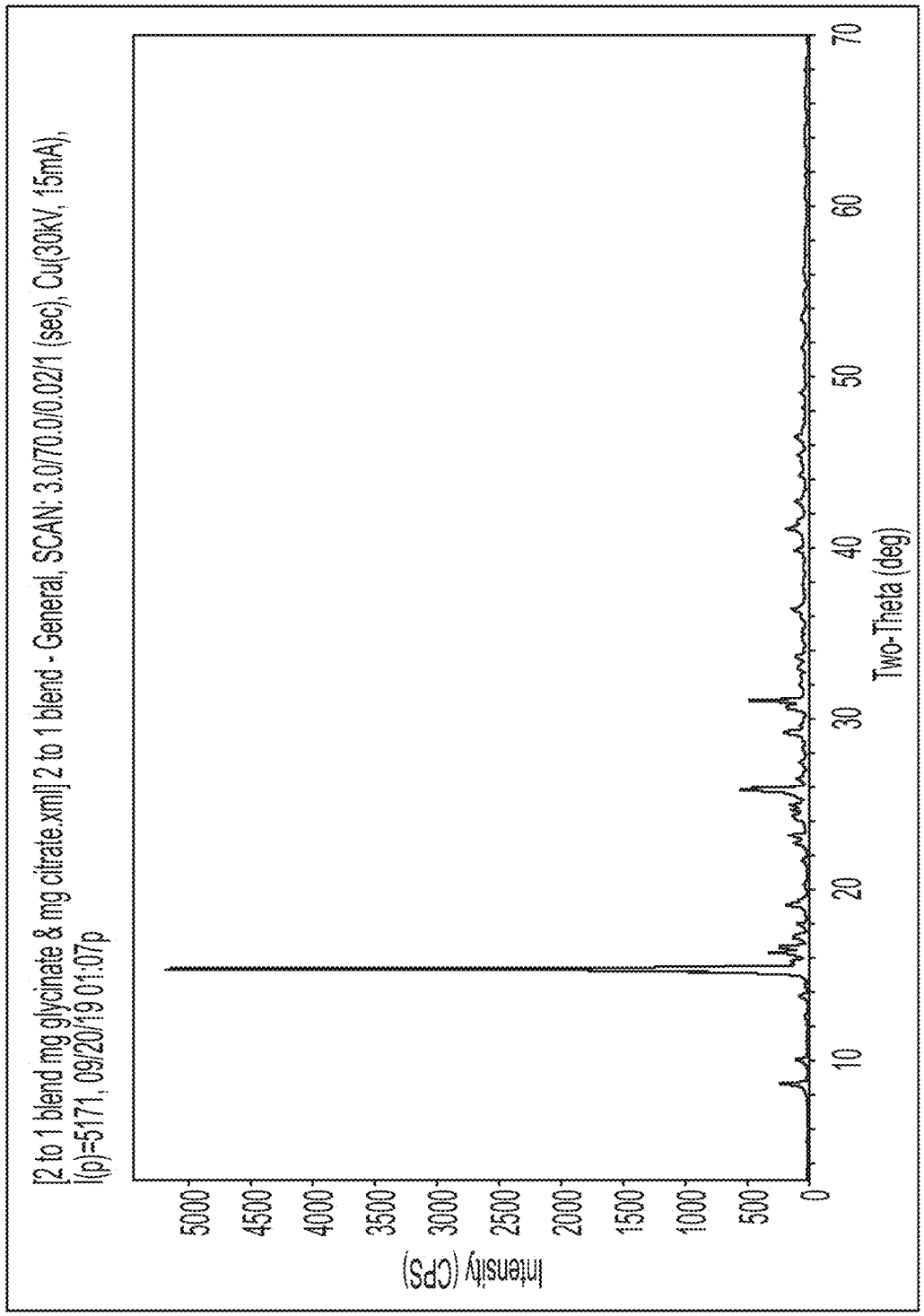

Likewise, the "component dry blend" described above displays distinct XRD patterns consistent with both magnesium bis-glycinate and magnesium citrate tribasic as shown in FIG. 14.

Figure 15:
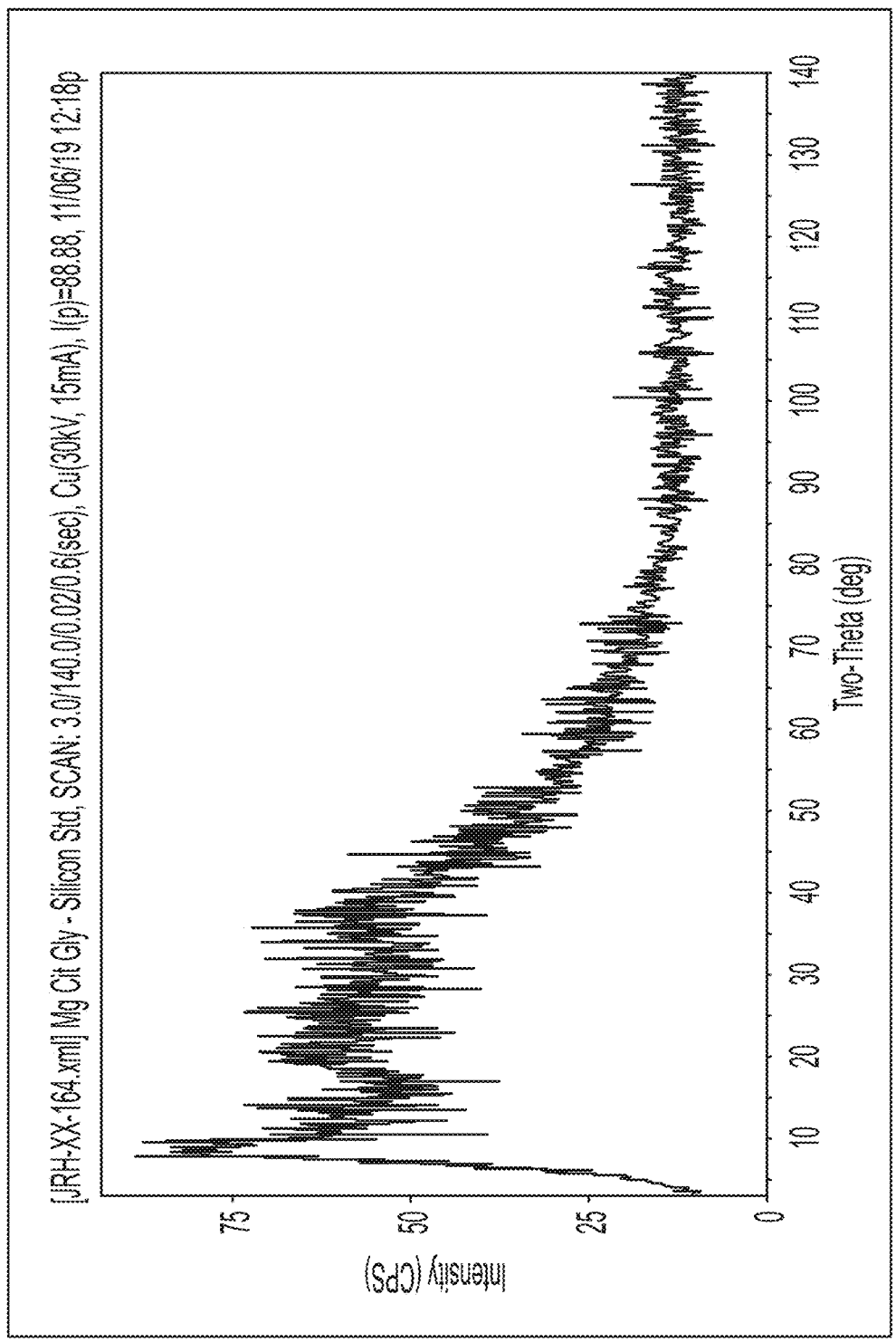
FIG. 15 shows the XRD pattern for the magnesium citrate glycinate co-salt sample.

Due to the amorphous nature of magnesium citrate glycinate co-salt as described in Particle Morphology by Scanning Electron Microscopy, this compound does not show any degree of crystallinity by XRD as shown in FIG. 15.

The fact that the "component dry blend" shows both magnesium bis-glycinate and magnesium citrate tribasic theta signals and the magnesium citrate glycinate co-salt does not, provides strong evidence that the co-salt is a unique entity (compound) and not a mere blend of components.

Aqueous Solubility

Magnesium glycinate is known to possess good aqueous solubility while magnesium citrate does not. Magnesium citrate glycinate co-salt exhibits excellent aqueous solubility unlike the "component dry blend" described above. To demonstrate, 10 g of magnesium citrate glycinate co-salt and 10 g of the "component dry blend" (FIG. 19) were simultaneously each added to 90 g DI water at room temperature. Once stirring was initiated, the magnesium citrate glycinate co-salt sample almost instantly went into solution while the "component dry blend" sample was an insoluble slurry (FIG. 20). After 5 minutes of stirring, the magnesium citrate glycinate co-salt sample had affected a clear and colorless solution while the "component dry blend" sample remained a slurry.

The clear and colorless 10% w/w solution of magnesium citrate glycinate co-salt was allowed to sit for 24 hours. Inspection (FIG. 21) of the co-salt sample solution yielded no change in the clear and colorless moniker put on the initial solution thereby demonstrating the aqueous stability of the magnesium citrate glycinate co-salt Compressibility Compressibility of a second sample of magnesium citrate glycinate was evaluated using an instrumented Carver press. Approximately 1.6 g, 5 mm thick tablets were compressed using the 0.4"×0.9" rectangular tooling. No excipients were used. The sides of the tooling were slightly dusted with magnesium stearate in order to facilitate tablet ejection and eliminate sticking. The tablets were subjected to a three-point bend stress using a TA.XT2-Plus texture analyzer (from Stable Micro Systems of Surrey, England). Flexural strength and young modulus of the compact were measured. In addition, compact density was calculated from the weight and size measurements of the tablets.

An attempt was made to compare compressibility of magnesium citrate glycinate with those of individual salts, magnesium citrate tribasic and magnesium bis-glycinate. However, these materials were characterized by inadequate compressibility and no cohesive tablets were obtained under the current experimental conditions.

Figure 22:
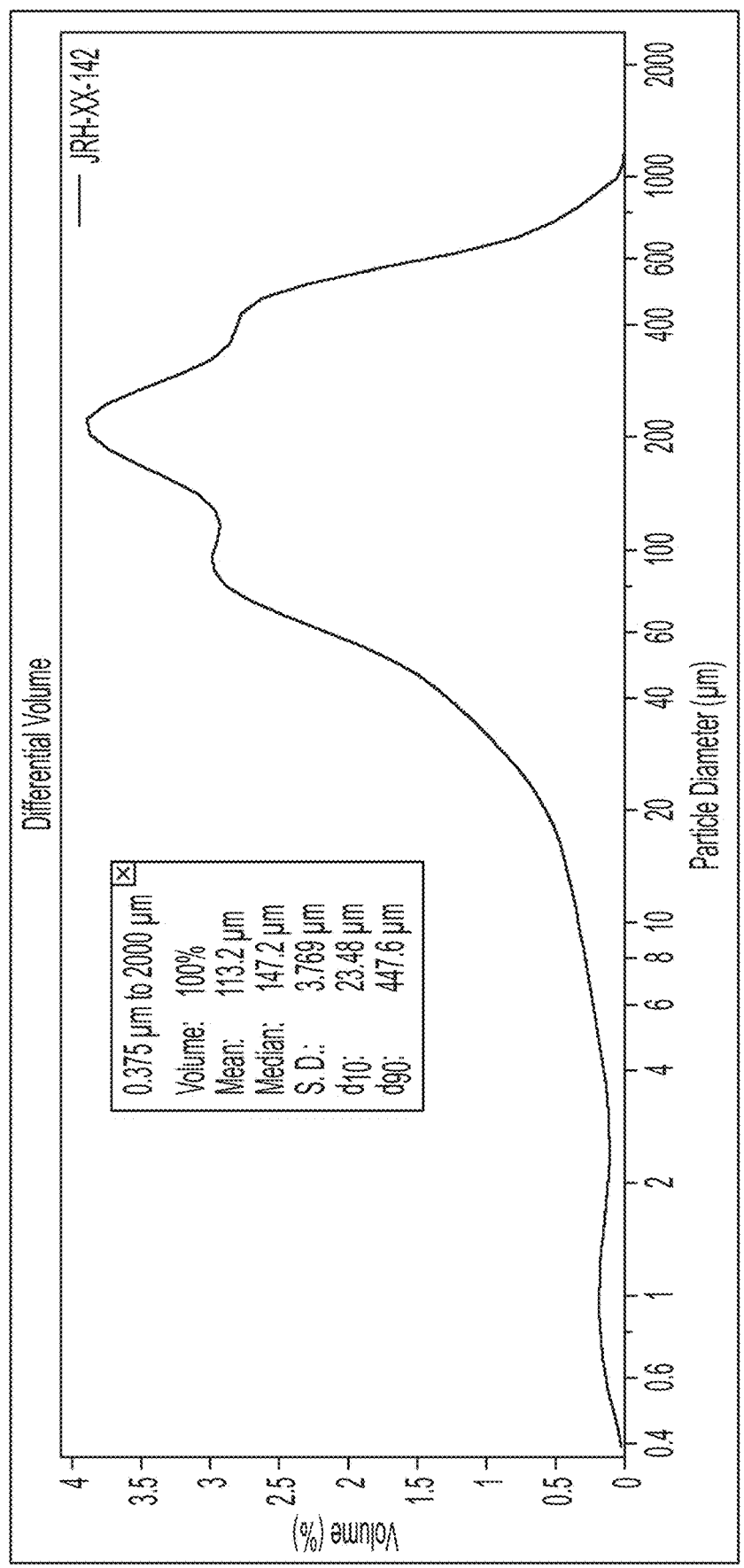
FIG. 22 is a graph of particle size distribution of the magnesium citrate glycinate co-salt sample.

In addition, particle size distribution and apparent density of di-magnesium citrate glycinate co-salt were measured. Particle size distribution of the second sample of di-magnesium citrate glycinate is shown in FIG. 22.

Magnesium citrate glycinate co-salt is characterized by apparent density of 1740 kg/m$^3$.

Figure 23:
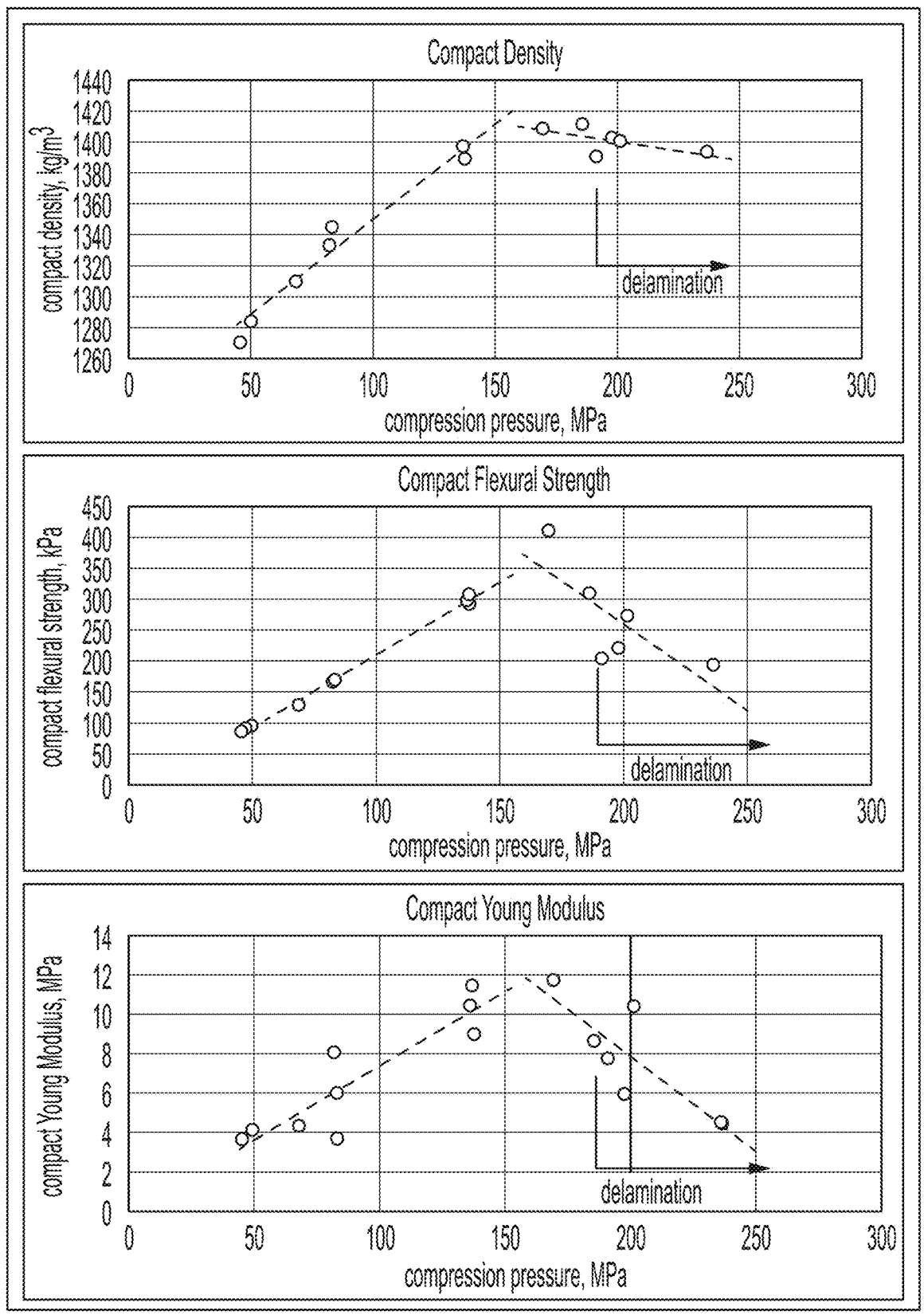
FIG. 23 contains compression profiles of the magnesium citrate glycinate co-salt sample.

Compression profiles of the tablets are shown in the FIG. 23.

At the higher pressures the product is over-compressed, however magnesium citrate glycinate co-salt is compressible in the range of compression pressures from approximately 50 MPa to approximately 150 MPa. The individual citrate and glycine salts failed to tablet as mention earlier.

Organoleptic Properties

Bis-Glycinate salts generally taste rather unfavorably and often are used in conjunction with flavor masking agents to achieve a palatable end product. An internal taste testing panel has confirmed that the taste profile of the magnesium citrate glycinate co-salt is far superior to the individual magnesium bis-glycinate.

EXAMPLES

The first two examples demonstrate the preparation of the magnesium citrate glycinate co-salt.

Example 1: Lab Scale Preparation of Magnesium Citrate Glycinate Co-Salt

An aqueous reaction mixture was prepared comprising 96.2 g anhydrous citric acid and 37.5 g glycine dissolved in 1000 g of water. The aqueous reaction mixture was heated to between about 60° C.-80° C. The resulting acid solution was neutralized with 40.3 g of magnesium oxide and adjusted to a pH between about 8.5-10.5 during a 4-8-hour digestion between about 60° C.-80° C. Once the pH had stabilized, the resulting reaction mass contained 155.9 g of magnesium citrate glycinate co-salt having a metal to ligand ratio of 1:1 remaining in solution. The reaction mass was filtered to remove any unreacted magnesium oxide and other extraneous matter. The filtrate was dried to produce a free-flowing powder containing magnesium citrate glycinate co-salt having a metal to ligand ratio of 1:1 and a moisture content of between 0.0-20.0%.

Example 2: Pilot Plant Scale Preparation of Magnesium Citrate Glycinate Co-Salt An aqueous reaction mixture was prepared comprising 2.41 Kg anhydrous citric acid and 0.94 Kg glycine dissolved in 25 Kg of water. The mixture was heated to between about 60° C.-80° C. The resulting acid solution was neutralized with 1.1 Kg of magnesium oxide and adjusted to a pH between about 8.5-10.5 during a 4-8-hour digestion at about 60° C.-80° C. Once the pH had stabilized, the resulting reaction mass contained 3.90 Kg of magnesium citrate glycinate co-salt having a metal to ligand ratio of 1:1 remaining in solution. The reaction mass was filtered to remove any unreacted magnesium oxide and other extraneous matter. The filtrate was dried to produce a free-flowing powder containing magnesium citrate glycinate co-salt having a metal to ligand ratio of 1:1 and a moisture content of 0.0-20.0%.

It was initially thought that the same process could be used to prepare similar co-salts with other di-valent metals, such as zinc, calcium, iron (ferrous), strontium, chromium, copper, nickel, manganese, and molybdenum. However, as shown in the Examples 3-7 below, attempts to produce calcium, copper, zinc, ferrous, and manganese citrate glycinate co-salts did not work. These salts will, if producible, will need to be produced by another route.

Example 3: Lab Scale Preparation of Calcium Citrate Glycinate Co-Salt

Figure 16:
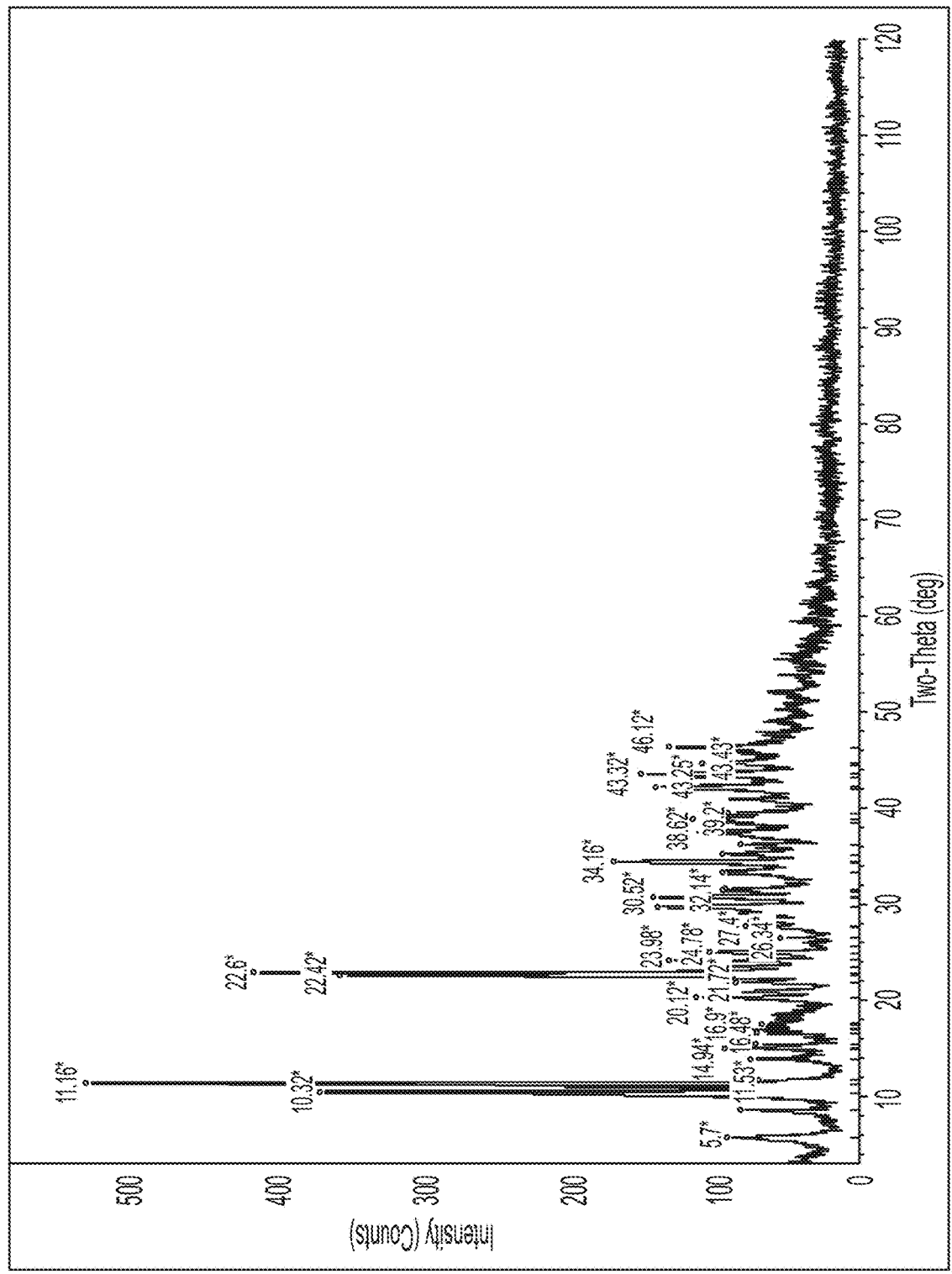
FIGS. 16-18 show the XRD patterns for failed attempts to produce calcium citrate glycinate, copper citrate glycinate and zinc citrate glycinate, respectively.

An aqueous reaction mixture was prepared comprising 96.2 g anhydrous citric acid and 37.5 g glycine dissolved in 1000 g of water. The mixture was heated to about 60° C.-80° C. The resulting acid solution was neutralized with 74.1 g of calcium hydroxide and adjusted to a pH between 8.5-10.5 during a 4-8-hour digestion at about 60° C.-80° C. Once the pH had risen above approximately 4.8, the reaction mass produced copious white precipitate. The reaction mass was filtered to isolate the precipitate. The precipitate was dried to produce a free-flowing powder containing only calcium citrate, shown by XRD (see FIG. 16). The desired calcium citrate glycinate co-salt was not produced.

Example 4: Lab Scale Preparation of Copper Citrate Glycinate Co-Salt

Figure 17:
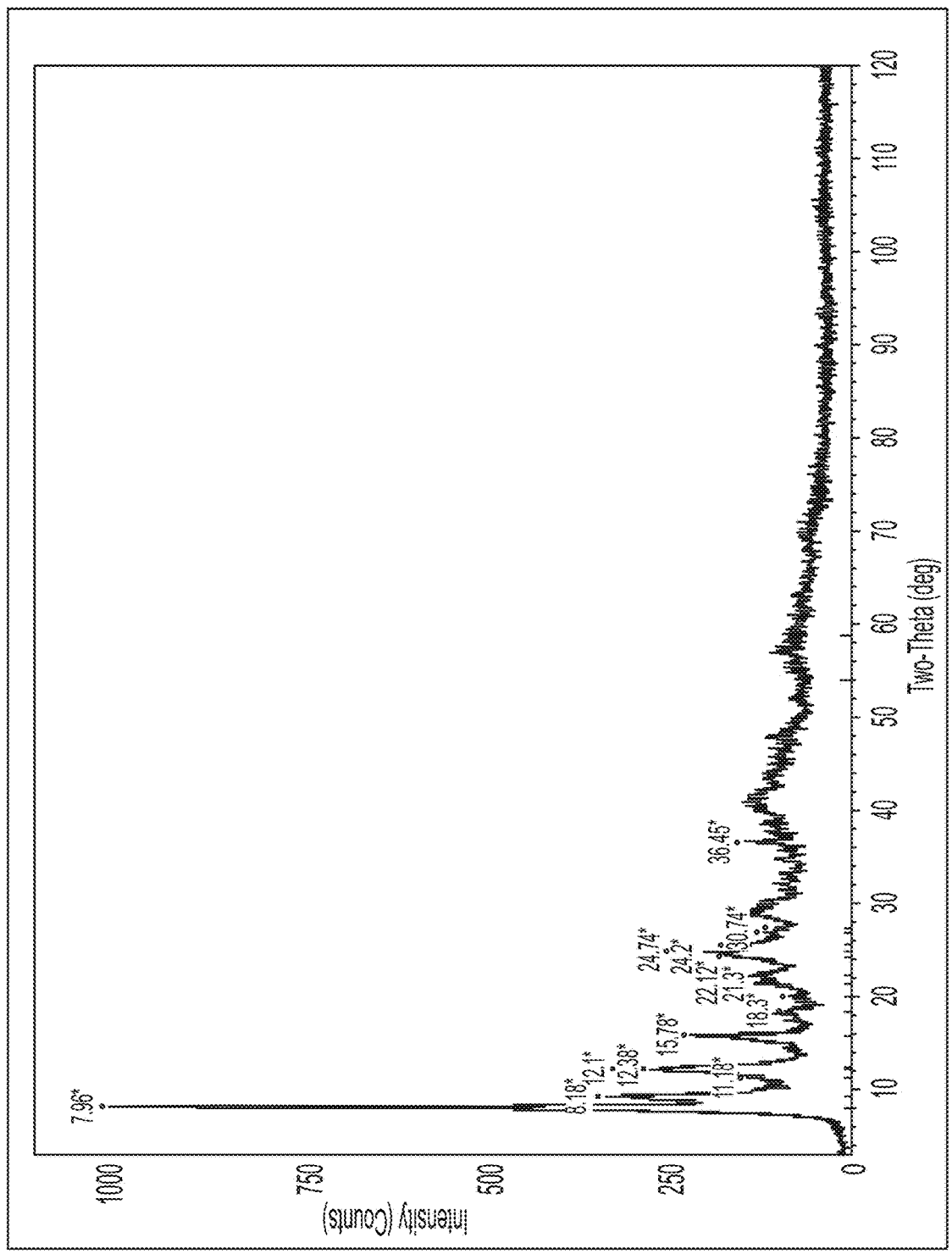

An aqueous reaction mixture was prepared comprising 96.2 g anhydrous citric acid and 37.5 g glycine dissolved in 1000 g of water. The mixture was heated to about 60° C.-80° C. The resulting acid solution was neutralized with 110.6 g of basic copper carbonate and adjusted to a pH between 8.5-10.5 during a 4-8-hour digestion at about 60° C.-80° C. Once the pH had risen above approximately 4.8, the reaction mass produced copious blue/green precipitate. The reaction mass was filtered to isolate the precipitate. The precipitate was dried to produce a free-flowing powder containing only copper citrate, shown by XRD (see FIG. 17). The desired copper citrate glycinate co-salt was not produced.

Example 5: Lab Scale Preparation of Zinc Citrate Glycinate Co-Salt

Figure 18:
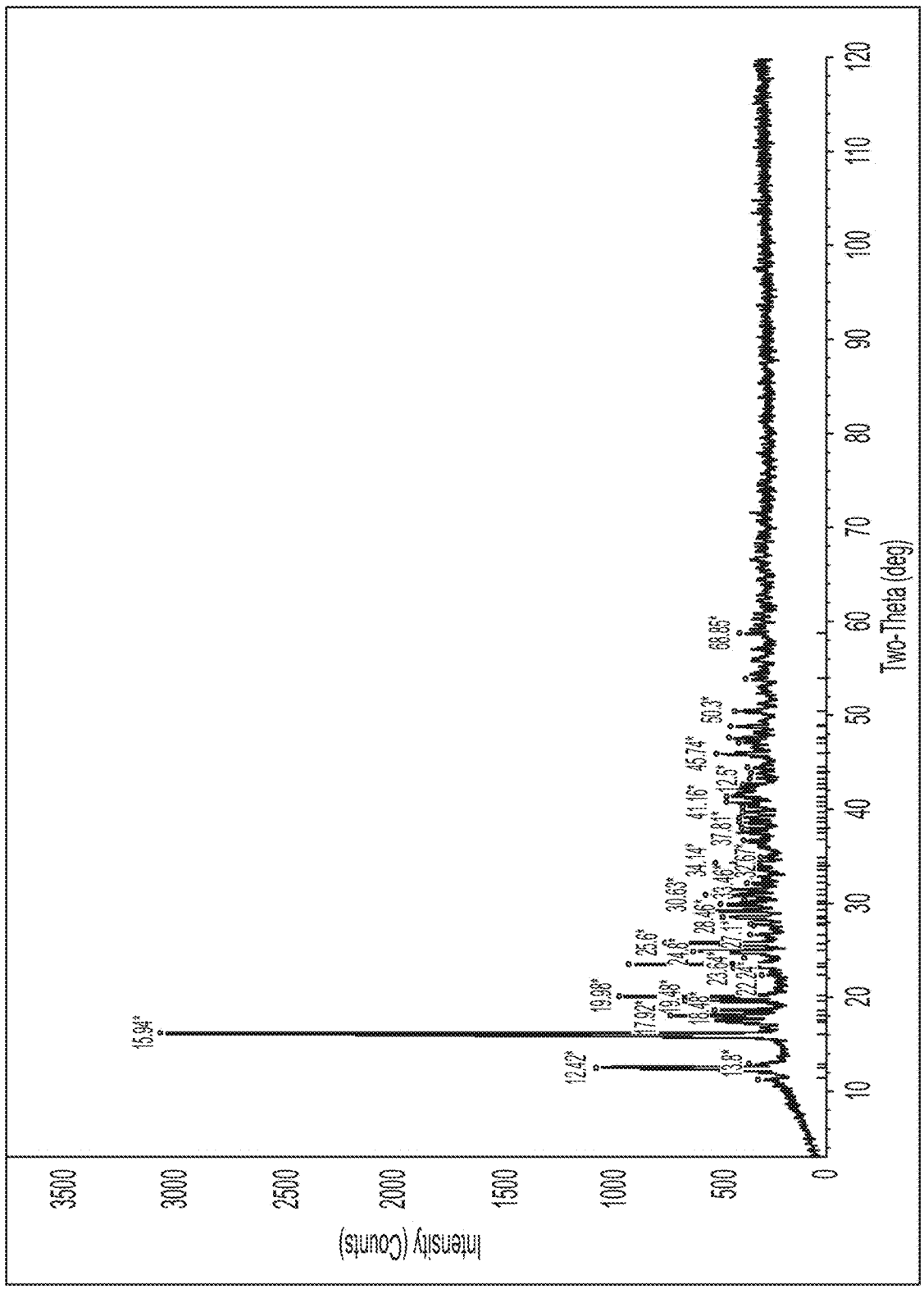

An aqueous reaction mixture was prepared comprising 96.2 g anhydrous citric acid and 37.5 g glycine dissolved in 1000 g of water. The mixture was heated to about 60° C.-80° C. The resulting acid solution was neutralized with 81.4 g of zinc oxide and adjusted to a pH between 8.5-10.5 during a 4-8-hour digestion at about 60° C.-80° C. Once the pH had risen above approximately 4.8, the reaction mass produced copious white precipitate. The reaction mass was filtered to isolate the precipitate. The precipitate was dried to produce a free-flowing powder containing only zinc citrate, shown by XRD (see FIG. 18). The desired zinc citrate glycinate co-salt was not produced.

Example 6: Lab Scale Preparation of Ferrous Citrate Glycinate Co-Salt

An aqueous reaction mixture was prepared comprising 96.2 g anhydrous citric acid and 37.5 g glycine dissolved in 1000 g of water. The mixture was heated to about 60° C.-80° C. The resulting acid solution was neutralized with 55.85 g of iron powder and adjusted to a pH between 8.5-10.5 during a 4-8-hour digestion at about 60° C.-80° C. Once the pH had risen above approximately 7.0, the reaction mass darkened significantly, as the iron(II) was oxidized to iron (III). The reaction was terminated as the desired ferrous citrate glycinate would not be produced at 100% purity due to oxidation of the iron.

Example 7: Lab Scale Preparation of Manganese Citrate Glycinate Co-Salt

An aqueous reaction mixture was prepared comprising 96.2 g anhydrous citric acid and 37.5 g glycine dissolved in 1000 g of water. The mixture was heated to about 60° C.-80° C. The resulting acid solution was neutralized with 54.9 g of manganese powder and adjusted to a pH between 8.5-10.5 during a 4-8-hour digestion at about 60° C.-80° C. Once the pH had risen above approximately 6.0, the reaction mass darkened significantly, as the manganese(II) was oxidizing and producing insoluble manganese dioxide precipitate. The reaction was terminated as the desired divalent manganese citrate glycinate would not be produced at 100% purity due to oxidation of the manganese.

In view of the above, it will be seen that the several objects and advantages of the present invention have been achieved and other advantageous results have been obtained.

As various changes could be made in the above constructions without departing from the scope of the invention, it is intended that all matter contained in the above description or shown in the accompanying drawings shall be interpreted as illustrative and not in a limiting sense.

The invention claimed is:

1. A magnesium citrate glycinate co-salt having a formula of $Mg_2C_8H_9NO_9$ and a structure of:

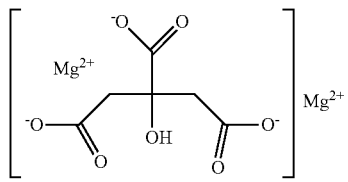

-continued

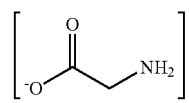

and hydrates thereof.

2. The magnesium citrate glycinate co-salt of claim 1 wherein the magnesium citrate glycinate co-salt has an apparent density of 1740 kg/m$^3$.

3. The magnesium citrate glycinate co-salt of claim 1 wherein the magnesium citrate glycinate co-salt is compressible in a range of compression pressures from approximately 50 MPa to approximately 150 MPa.

4. A method of producing the magnesium citrate glycinate co-claim 1 comprising forming an aqueous reaction mixture of citric acid and glycine in a 1:1 molar ratio and neutralizing the aqueous reaction mixture with a magnesium source, the aqueous reaction mixture having a magnesium:citrate:glycinate molar ratio of 2:1:1.

5. The method of claim 4 wherein the magnesium source is magnesium, a magnesium oxide, a magnesium hydroxide, or a magnesium carbonate, the overall reaction for producing the co-salt being:

$$2Mg + C_6H_8O_7 + C_2H_5NO_2 \rightarrow Mg_2C_8H_9NO_{9(aq)} + 2H_{2(g)}$$

—or—

$$2MgO + C_6H_8O_7 + C_2H_5NO_2 \rightarrow Mg_2C_8H_9NO_{9(aq)} + 2H_2O_{(l)}$$

—or—

$$2Mg(OH)_2 + C_6H_8O_7 + C_2H_5NO_2 \rightarrow Mg_2C_8H_9NO_{9(aq)} + 4H_2O_{(l)}$$

—or—

$$2MgCO_3 + C_6H_8O_7 + C_2H_5NO_2 \rightarrow Mg_2C_8H_9NO_{9(aq)} + 2H_2O_{(l)} + 2CO_{2(g)}.$$

6. The method of claim 4 wherein the aqueous reaction mixture of 1:1 molar ratio of citric acid and glycine is neutralized to a pH between 8.5-10.5 to form a neutralized solution.

7. The method of claim 6 wherein the step of neutralizing the aqueous reaction mixture is carried out over a 4-8-hour digestion period at between about 60° C.-80° C.

8. The method as in claim 4 where the neutralized solution is dried to a free-flowing powder.

* * * * *